May 14, 1940. M. OKADA Plant Pat. 399
RED CARNATION
Filed May 22, 1939
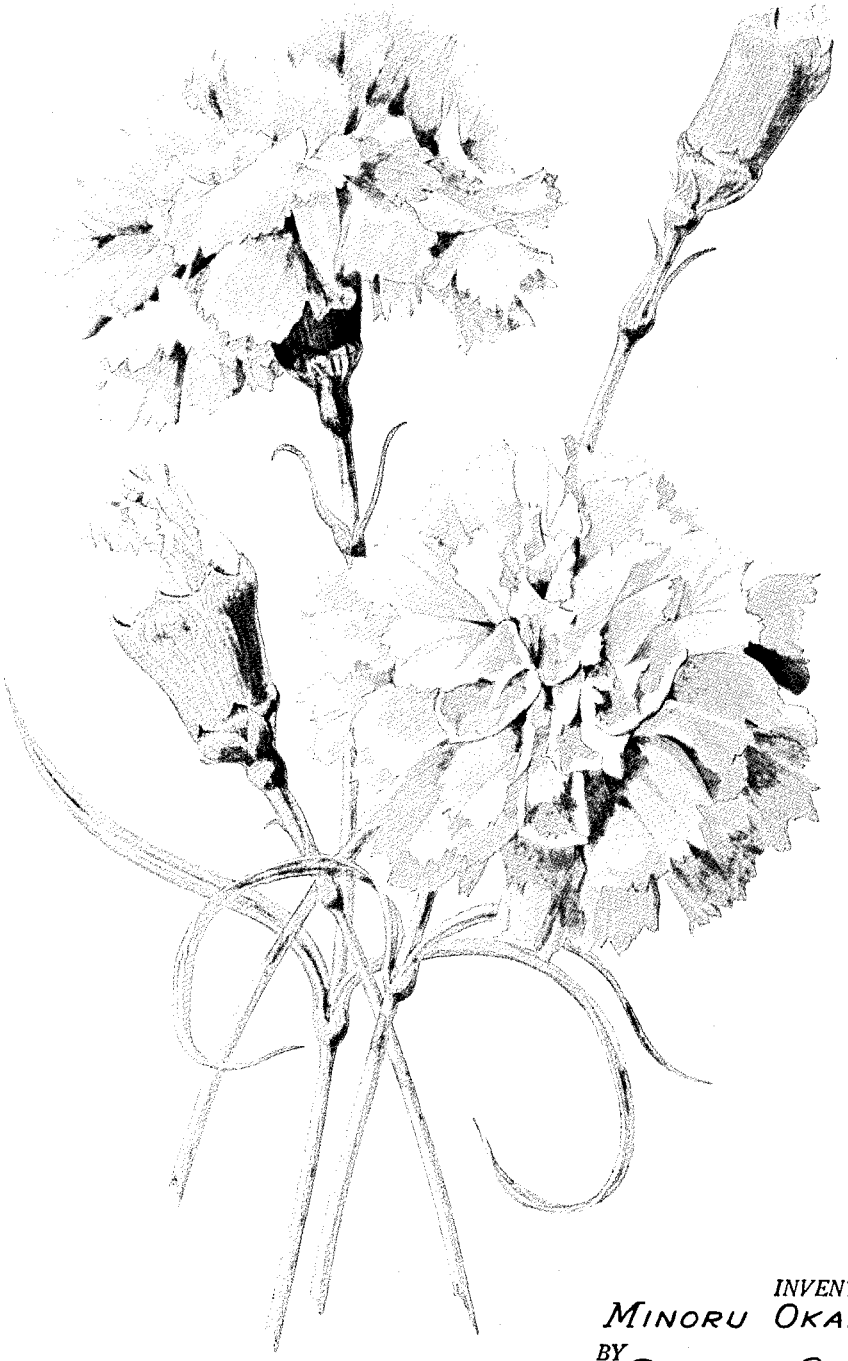
INVENTOR.
MINORU OKADA
BY Oscar A. Mellin
ATTORNEY Patented May 14, 1940

Plant Pat. 399

UNITED STATES PATENT OFFICE

399

RED CARNATION

Minoru Okada, San Lorenzo, Calif.

Application May 22, 1939, Serial No. 275,029

1 Claim. (Cl. 47—60)

This invention relates generally to carnations of the greenhouse forcing type and particularly pertains to a carnation of a novel color and size.

The outstanding characteristics of my new variety of carnation are the distinctive color of the blossom, the extremely large size, and the high center caused by peculiar petal arrangement.

I originated this variety by crossing carnation "Spectrum Supreme," which is of a dark red color, and carnation "Abundant," which is of a pink color, neither color in any manner approaching the color of my present new variety. The carnation known as "Abundant" is the seed bearing parent.

My new variety of carnation is illustrated in approximately natural size and in approximately natural color in the original drawing, which includes a side view and a front view of an open blossom and views of partly open buds.

I have asexually reproduced my new variety over a period of approximately two years and its characteristics have persisted without change.

The plant itself is a vigorous one, reaching a height in excess of 40 inches with strong stiff stems deep dull yellow green in color changing to dark yellow green in color from one node to the next above succeeding node covered with a grayish bloom. The color of the stem corresponds approximately to the color Deep Dull Yellow Green #1 and Dark Dull Yellow Green, set out on Plate #XXXII in Ridgway's "Color Standards and Color Nomenclature." The leaves are of a deep green corresponding to Empire Green, set out in Ridgway's "Color Standards and Color Nomenclature," Plate #XXXII. The leaves are rather heavy and considerably curled, the lower ones averaging approximately ⅜ of an inch in width. The length of the leaves at the base of the stem is usually between five and six inches long, which leaves, of course, considerably reduce in length on the stem toward the blossom end. The leaves are inclined to be rather upright, although some of them noticeably curl slightly.

The buds are rather thick and heavy and the blossom is extremely large, being between 4¼ and 5 inches in diameter, with approximately 50 to 55 petals. These petals are rather irregularly serrated at their edges and very gently ruffled. The shanks of the petals are of medium length comprising less than half the total length of the petal.

The color of the blossom is extremely close to that labeled Spectrum Red in Ridgway's "Color Standards and Color Nomenclature." The accompanying illustration approaches the exact color of the blossom, but due to the impossibility of the artist exactly reproducing the color, I have referred to the color in Ridgway's "Color Standards and Color Nomenclature" as above.

The calyx consists of a single tube 1¼ inches long by one inch in diameter divided into five lobes. It is extremely strong and does not split. It is of a slightly lighter green color than the stems.

The blossom has a mild pleasant fragrance.

The ovary is of a medium size of approximately ½ of an inch long, which is set into a pithy cup about ¼ of an inch high. The hard case of the ovary encloses many ovules. The styles set upon the top of the ovary are usually three but sometimes four in number and being approximately ¾ of an inch long. The styles project directly from the end of the ovary with the base of the styles arranged closely together in circular fashion about the end of the ovary. The outer ends of the styles are usually divided into two stigmas. These are white turning to Eosine Pink (Plate #1, Ridgway's "Color Standards and Color Nomenclature") at the terminals of the stigmas which are slightly curled at their ends. The overall length of the entire pistil is about 1¼ inches.

The stamens arise from the edge of the pithy cup and are approximately fifteen in number and are rather regular, and of more or less uniform lengths and are topped by small anthers. The color of the filaments of the stamens is white and the anthers are white with a slight tinge of green at the top, but there is no color chart in Ridgway's "Color Standards and Color Nomenclature" closely corresponding to this color.

Having thus described my invention, what I claim and desire to secure by Letters Patent is:

A new variety of carnation substantially as illustrated and described characterized particularly by the distinctive color and the extreme large size of its blossom as illustrated and described.

MINORU OKADA.